(12) United States Patent
Kimura et al.

(10) Patent No.: US 10,278,604 B2
(45) Date of Patent: *May 7, 2019

(54) FETAL STATE ESTIMATION APPARATUS, FETAL STATE ESTIMATING METHOD, AND NON-TRANSITORY COMPUTER-READABLE MEDIUM

(71) Applicant: TOHOKU UNIVERSITY, Sendai-shi, Miyagi (JP)

(72) Inventors: Yoshitaka Kimura, Sendai (JP); Naoaki Sato, Sendai (JP); Nobuo Yaegashi, Sendai (JP); Takuya Ito, Sendai (JP); Miyuki Endo, Sendai (JP); Sayaka Oshio, Sendai (JP); Hidekazu Nishigori, Sendai (JP); Yuji Nabeshima, Sendai (JP); Mitsuyuki Nakao, Sendai (JP)

(73) Assignee: TOHOKU UNIVERSITY, Sendai-shi, Miyagi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/273,985

(22) Filed: Sep. 23, 2016

(65) Prior Publication Data

US 2017/0007143 A1 Jan. 12, 2017

Related U.S. Application Data

(63) Continuation of application No. PCT/JP2014/058586, filed on Mar. 26, 2014.

(51) Int. Cl.
*A61B 5/04* (2006.01)
*A61B 5/0444* (2006.01)
(Continued)

(52) U.S. Cl.
CPC ........ *A61B 5/0444* (2013.01); *A61B 5/04028* (2013.01); *A61B 5/0456* (2013.01);
(Continued)

(58) Field of Classification Search
CPC ........................... A61B 5/0444; A61B 5/1121
See application file for complete search history.

(56) References Cited

U.S. PATENT DOCUMENTS

2007/0213627 A1 9/2007 James et al.
2008/0146953 A1 6/2008 Kimura et al.
(Continued)

FOREIGN PATENT DOCUMENTS

JP 2002-538872 A 11/2002
JP 2006-204759 A 8/2006
(Continued)

OTHER PUBLICATIONS

Notification of Reasons for Refusal issued by the Japan Patent Office for corresponding Japanese Patent Application No. 2016-509716, dated Oct. 17, 2017, with an English translation.
Sameni et al., "Multichannel ECG and noise modeling: Application to maternal and fetal ECG signals" EURASIP Journal on Advances in Signal Processing, 2007, Article ID 43407.
(Continued)

*Primary Examiner* — Eric D. Bertram
(74) *Attorney, Agent, or Firm* — Myers Wolin, LLC

(57) ABSTRACT

A fetal state estimation apparatus estimates a state of a fetus in a maternal body based on a potential signal indicating a change in potential on a surface of the maternal body. The fetal state estimation apparatus is configured to include a rotation angle estimation unit which estimates a rotation angle of the fetus with respect to the maternal body at every beating of a heart of the fetus based on the potential signal and a fetal movement estimation unit which estimates a fetal movement which is a movement of the fetus based on the potential signal and the estimated rotation angle.

10 Claims, 11 Drawing Sheets

(51) Int. Cl.
    *A61B 5/0456* (2006.01)
    *A61B 5/11* (2006.01)
    *A61B 5/0402* (2006.01)
    *A61B 5/00* (2006.01)
    *A61B 5/0245* (2006.01)

(52) U.S. Cl.
    CPC .............. *A61B 5/11* (2013.01); *A61B 5/1118* (2013.01); *A61B 5/1121* (2013.01); *A61B 5/7278* (2013.01); *A61B 5/0245* (2013.01)

(56) References Cited

U.S. PATENT DOCUMENTS

| | | |
|---|---|---|
| 2009/0259133 A1 | 10/2009 | Wolfberg et al. |
| 2010/0185108 A1* | 7/2010 | Vullings ............ A61B 5/04011 600/511 |
| 2011/0092837 A1 | 4/2011 | Lee et al. |
| 2012/0150010 A1 | 6/2012 | Hayes-Gill et al. |

FOREIGN PATENT DOCUMENTS

| | | |
|---|---|---|
| JP | 2011-516238 A | 5/2011 |
| JP | 2013-505032 A | 2/2013 |
| WO | 00/54650 A2 | 9/2000 |

OTHER PUBLICATIONS

International Search Report issued for corresponding International Patent Application No. PCT/JP2014/058586, dated Jun. 17, 2014.

\* cited by examiner

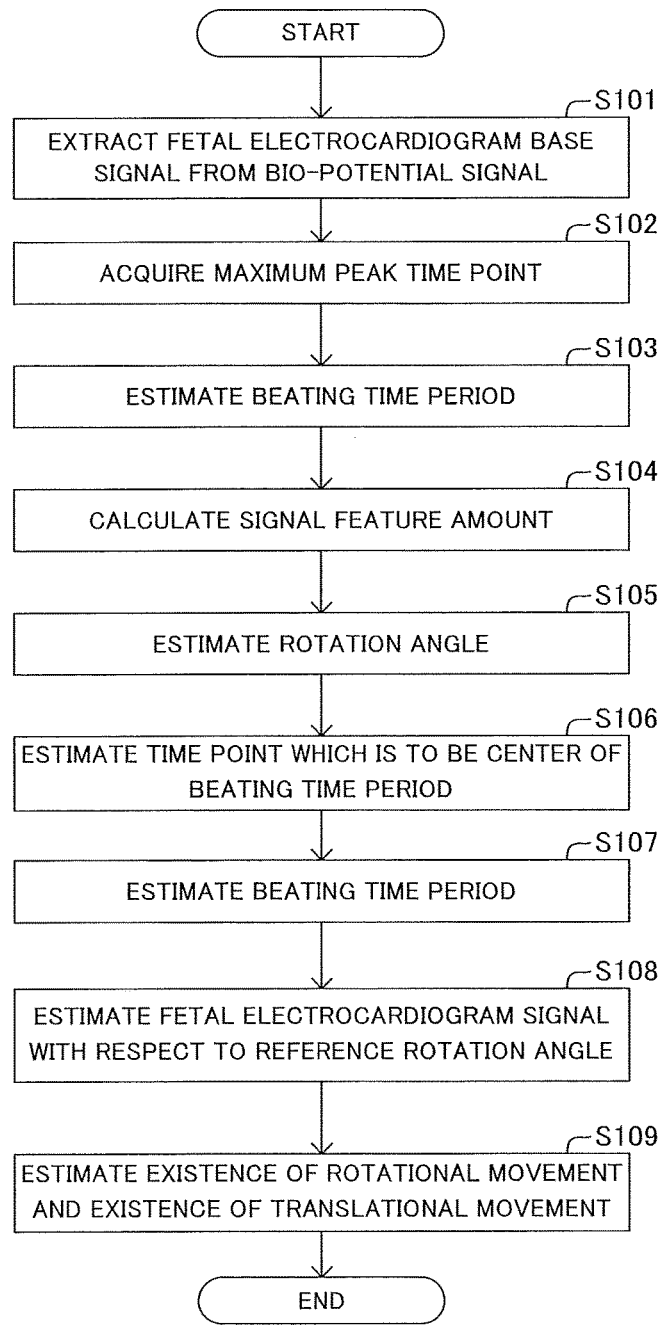

FETAL STATE ESTIMATION APPARATUS, FETAL STATE ESTIMATING METHOD, AND NON-TRANSITORY COMPUTER-READABLE MEDIUM

CROSS-REFERENCE TO RELATED APPLICATION

The present application is a continuation application of International Application No. PCT/JP2014/058586, filed on Mar. 26, 2014. The contents of this application are incorporated herein by reference in their entirety.

FIELD

The present invention relates to a fetal state estimation apparatus, a fetal state estimating method, and a fetal state estimating program.

BACKGROUND

There is known an electrocardiogram estimation apparatus which estimates an electrocardiogram signal indicating a change in electromotive force of heart by attaching electrodes to a surface of a human body and measuring a potential signal indicating a change in potential on the surface of the human body through the electrodes.

As illustrated in FIG. 1, the electrocardiogram signal includes waves having peaks called a P wave WP, a Q wave WQ, an R wave WR, an S wave WS, and a T wave WT at every beating. Time periods between the peaks of each wave in the electrocardiogram signal are used for diagnosis, test, or the like of disease. The heart rate is measured, for example, by acquiring the time period between the peaks of consecutive R waves WR.

It is known that, in two states where positions of the electrodes with respect to the heart are different from each other, even in the case where a change in electromotive force of heart is the same, the appearing shapes of the change in electromotive force of heart in the measured potential signals are different from each other. FIG. 2 illustrates two potential signals C10 and C11 measured in the two states where the positions of the electrodes with respect to the heart are different from each other even in the case where the change in electromotive force of heart is the same. For example, as illustrated in FIG. 2, the magnitude and timing of peak of each wave is changed according to the position of the electrode with respect to the heart.

Since a fetus is accommodated in a maternal body, it is difficult to attach the electrodes to a surface of the body of the fetus. Therefore, for example, an electrocardiogram estimation apparatus disclosed in Patent Literature measures a potential signal indicating a change in potential on a surface of a maternal body through electrodes which are attached on the surface of the maternal body and estimates an electrocardiogram signal of a fetus based on the measured potential signal.

In addition, there is known a fetal state estimation apparatus which estimates a fetal movement which is a movement of a fetus by generating an ultrasonic wave on a surface of a maternal body and observing the Doppler's effect of reflected waves obtained by reflection of the generated ultrasonic wave on the fetus in the maternal body (for example, refer to Patent Literature 2).

Patent Literature 1: JP 2006-204759 A
Patent Literature 2: JP 2013-505032 W

SUMMARY

However, in the above-described fetal state estimation apparatus, the same Doppler's effect may be observed in both of the case where the fetus performs rotational movement and the case where the fetus performs translational movement with respect to the abdominal wall of the maternal body. Therefore, there is a problem in that it is not possible to estimate the fetal movement at a high accuracy.

In addition, for example, estimation of the existence of translational movement among the fetal movements based on the magnitude of peak of a specific wave in an electrocardiogram signal is considered. However, the fetus performs rotational movement with respect to the maternal body during a relatively short time period. Therefore, the appearing shape of the change in electromotive force of heart of the fetus in the potential signal measured through the electrodes attached to the surface of the maternal body is easily changed according to the rotation of the fetus. For this reason, in the case of using the above-described electrocardiogram estimation apparatus, there is a problem in that it is not possible to estimate the fetal movement at a high accuracy based on the potential signal measured through the electrodes attached to the surface of the maternal body.

An object of the present invention is to solve the above-described problem that it is not possible to estimate a fetal movement at a high accuracy.

According to an aspect of the present invention, there is provided a fetal state estimation apparatus which estimates a state of a fetus in a maternal body based on a potential signal indicating a change in potential on a surface of the maternal body.

Furthermore, the fetal state estimation apparatus is configured to include: a rotation angle estimation unit which estimates a rotation angle of the fetus with respect to the maternal body at every beating of a heart of the fetus based on the potential signal; and a fetal movement estimation unit which estimates a fetal movement which is a movement of the fetus based on the potential signal and the estimated rotation angle.

According to another aspect of the present invention, there is provided a fetal state estimating method for estimating a state of a fetus in a maternal body based on a potential signal indicating a change in potential on a surface of the maternal body.

Furthermore, the fetal state estimating method includes: estimating a rotation angle of the fetus with respect to the maternal body at every beating of a heart of the fetus based on the potential signal; and estimating a fetal movement which is a movement of the fetus based on the potential signal and the estimated rotation angle.

According to still another aspect of the present invention, there is provided a fetal state estimating program for causing a computer to execute a process of estimating a state of a fetus in a maternal body based on a potential signal indicating a change in potential on a surface of the maternal body.

Furthermore, the fetal state estimating program causes the computer to execute the process including: estimating a rotation angle of the fetus with respect to the maternal body at every beating of a heart of the fetus based on the potential signal; and estimating a fetal movement which is a movement of the fetus based on the potential signal and the estimated rotation angle.

According to a fetal state estimation apparatus disclosed, it is possible to estimate a fetal movement at a high accuracy.

BRIEF DESCRIPTION OF DRAWINGS

FIG. 14 is a flowchart illustrating an example of a process performed by the fetal state estimation apparatus illustrated in FIG. 3.

DESCRIPTION OF EMBODIMENTS

Hereinafter, embodiments of a fetal state estimation apparatus, a fetal state estimating method, and a fetal state estimating program according to the present invention will be described with reference to FIGS. 3 to 14.

First Embodiment (Configuration)

Figure 1:
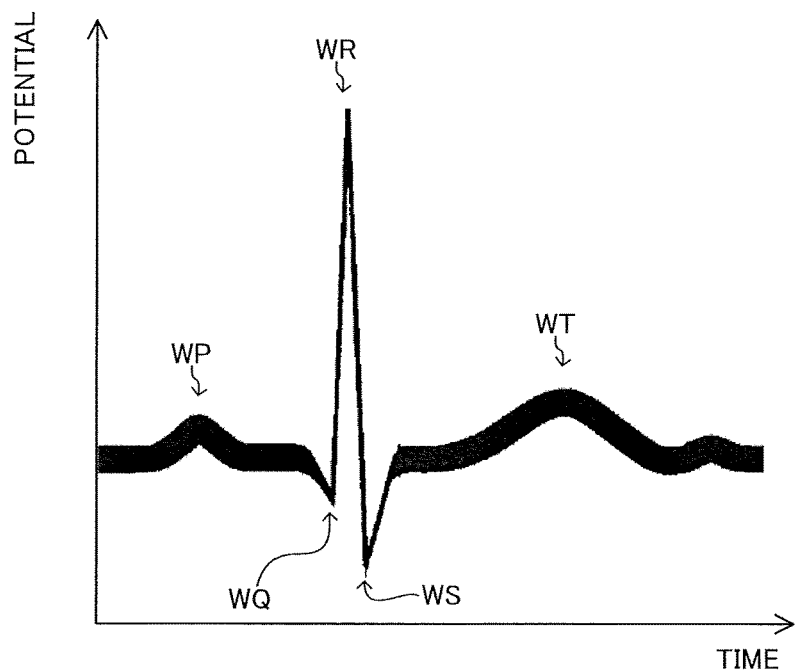
FIG. 1 is a diagram for illustrating an example of an electrocardiogram signal.
Figure 2:
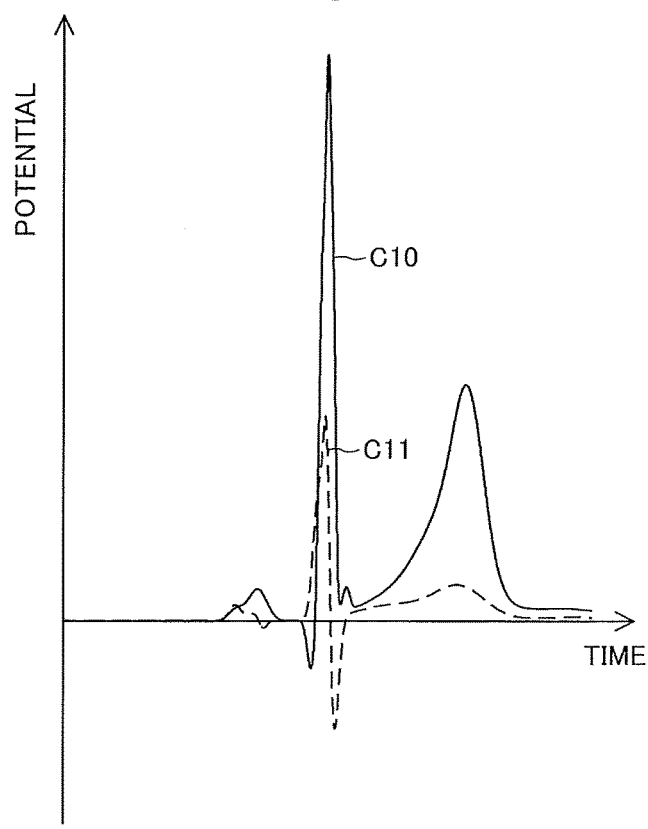
FIG. 2 is a graph illustrating an example of two potential signals measured in two states where positions of electrodes with respect to the heart are different from each other.
Figure 3:
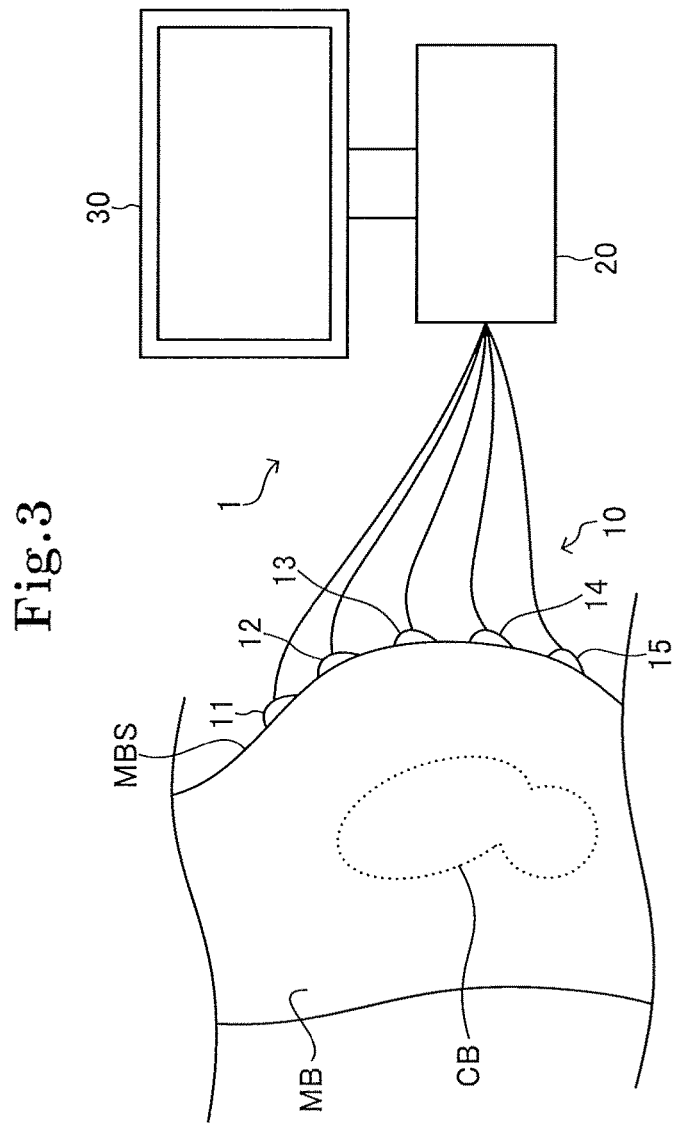
FIG. 3 is a diagram illustrating an example of a configuration of a fetal state estimation apparatus according to a first embodiment.

As illustrated in FIG. 3, a fetal state estimation apparatus 1 according to a first embodiment is configured to include a measurement unit 10, a processing unit 20, and an output unit 30.

The measurement unit 10 is configured to include electrodes 11 to 15. Although FIG. 3 illustrates an example where the measurement unit 10 includes five electrodes, the number of electrodes included in the measurement unit 10 may be four or less and six or more. The electrodes 11 to 15 are attached on a surface MBS (for example, skin) of the abdomen of a pregnant maternal body MB.

The measurement unit 10 measures a bio-potential signal indicating a change in potential on the surface MBS of the maternal body MB through the electrodes 11 to 15.

The bio-potential signal is a superposition of a maternal body electrocardiogram base signal caused by the beating of the heart of the maternal body MB, a maternal body electromyogram base signal caused by activity of muscle fibers of the maternal body MB, a fetal electrocardiogram base signal caused by the beating of the heart of the fetus CB accommodated in the uterus of the maternal body MB, noises, and the like.

Figure 4:
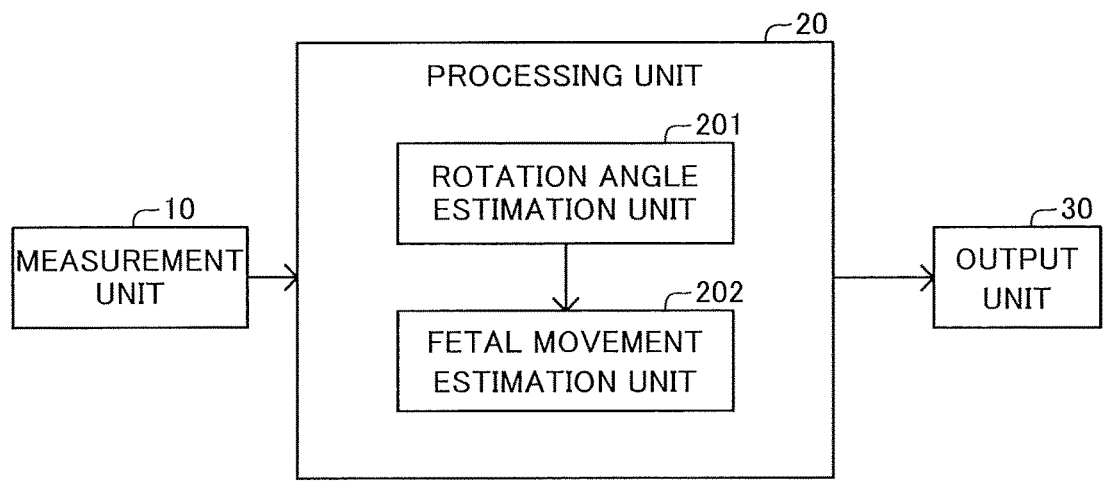
FIG. 4 is a block diagram illustrating an example of a function of a processing unit illustrated in FIG. 3.

The processing unit 20 processes the bio-potential signal measured by the measurement unit 10. As illustrated in FIG. 4, functions of the processing unit 20 include a rotation angle estimation unit 201 and a fetal movement estimation unit 202.

In the example, the processing unit 20 is configured to include a processing device (for example, a CPU (Central Processing Unit), a DSP (Digital Signal Processor), or the like) and a storage device, and implements the functions by causing the processing device to execute a fetal state estimating program stored in the storage device in advance. The processing unit 20 may implement at least a portion of the functions using an integrated circuit (for example, LSI (Large Scale Integration) or the like).

The rotation angle estimation unit 201 extracts a fetal electrocardiogram base signal from a bio-potential signal measured by the measurement unit 10 using an Independent Component Analysis (ICA).

For example, the ICA is a natural gradient method, a Fast ICA method, or a reference-based ICA method. As disclosed in Patent Literature 1, the reference-based ICA method is a method of generating a reference signal based on a beating period signal indicating a period of beating of the heart of the fetus and extracting a fetal electrocardiogram base signal from a bio-potential signal based on the generated reference signal. Herein, the beating period signal may also be generated based on the bio-potential signal. In addition, the beating period signal may also be a signal measured by an ultrasonic sensor.

The rotation angle estimation unit 201 may also extract the fetal electrocardiogram base signal after performing a reduction process of reducing the maternal body electrocardiogram base signal from the measured bio-potential signal. In this case, for example, the rotation angle estimation unit 201 may estimate the maternal body electrocardiogram base signal through the electrodes (not shown) attached to the chest of the maternal body MB, and may perform the reduction process based on the estimated maternal body electrocardiogram base signal.

In addition, the rotation angle estimation unit 201 may extract the fetal electrocardiogram base signal after reducing the noise by applying a band pass filter. For example, the rotation angle estimation unit 201 may use a band pass filter having a band from 20 Hz to 30 Hz as a pass band.

Since the rotation angle of the fetus CB with respect to the maternal body MB is changed according to time elapse, the appearing shape of the change in electromotive force of heart of the fetus CB in the fetal electrocardiogram base signal is changed according to time elapse. Therefore, the magnitude of peak of the R wave in a time period when the rotational movement among the fetus movements is performed is also easily changed. For this reason, it is difficult to estimate the existence of translational movement among the fetal movements with sufficiently high accuracy based on the change in magnitude of peak of the R wave.

The fetal state estimation apparatus 1 according to the first embodiment estimates the rotation angle of the fetus CB with respect to the maternal body MB and estimates the existence of translational movement among the fetal movements based on the estimated rotation angle and the fetal electrocardiogram base signal. Accordingly, it is possible to estimate the fetal movement with high accuracy.

In the example, the rotation angle estimation unit 201 estimates the rotation angle of the fetus CB with respect to the maternal body MB based on the extracted fetal electrocardiogram base signal. Hereinafter, the estimation of the rotation angle will be described.

Figure 5:
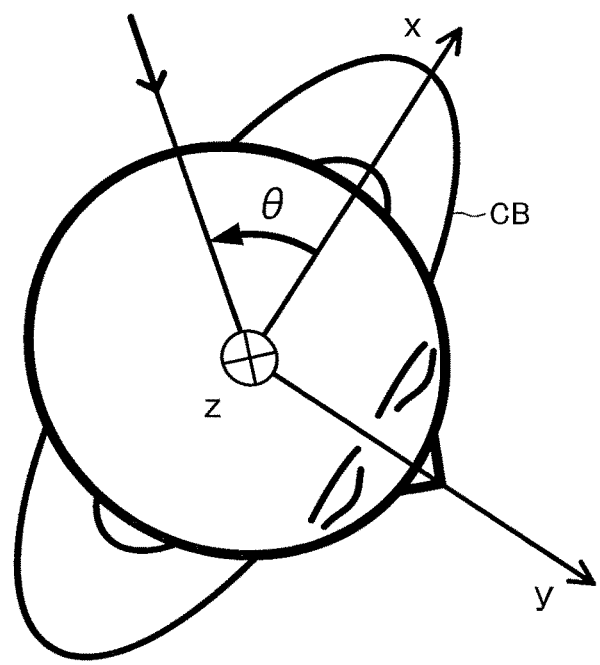
FIG. 5 is a diagram for illustrating an example of a coordinate system used by the fetal state estimation apparatus illustrated in FIG. 3.

First, a coordinate system will be described. In the example, as illustrated in FIG. 5, a right-handed rectangular coordinate system is used. In the rectangular coordinate system, the forward direction of the fetus CB is set to the y axis, the downward direction of the fetus CB is set to the z axis, and the leftward direction of the fetus CB is set to the x axis. The rotation angle θ with respect to the fetus CB is an angle rotated counterclockwise from the x axis as the fetus CB is seen in the positive direction of the z axis.

In the example, the case where the up/down direction of the fetus CB and the up/down direction of the maternal body MB are coincident with each other is assumed. Therefore, in the example, the rotational movement of the fetus CB is movement where the fetus CB rotates about the z axis as the central axis of rotation. The fetal state estimation apparatus 1 may also be applied to the case where the up/down direction of the fetus CB and the up/down direction of the maternal body MB are different from each other.

The fetal electrocardiogram signal $ECG_\theta(\tau)$ of the case where the fetus CB is seen in the direction obtained by rotating the negative direction of the x axis by the rotation angle θ is expressed by Mathematical Formula 1 based on the fetal electrocardiogram signal $ECG_x(\tau)$ of the case where the fetus CB is seen in the negative direction of the x axis, the fetal electrocardiogram signal $ECG_y(\tau)$ of the case where the fetus CB is seen in the negative direction of the y axis, and the rotation angle θ. τ denotes a time. The fetal electrocardiogram signal is an electrocardiogram signal of the fetus CB.

$ECG_\theta(\tau)=\cos(\theta)\cdot ECG_x(\tau)-\sin(\theta)\cdot ECG_y(\tau)$ [Mathematical Formula 1]

Herein, the fetal electrocardiogram signal $ECG_x(\tau)$ may be considered to be a signal indicating an electrocardiogram obtained by projecting a vector electrocardiogram on a left side surface of the fetus CB. The fetal electrocardiogram signal $ECG_y(\tau)$ may be considered to be a signal indicating an electrocardiogram obtained by projecting a vector electrocardiogram on a front surface of the fetus CB.

In the example, by using an ICA to extract the fetal electrocardiogram base signal, the fetal electrocardiogram base signal $u_\theta(\tau)$ extracted by the rotation angle estimation unit 201 is normalized so that the average value becomes 0 and the variance becomes 1.

The rotation angle estimation unit 201 estimates the beating time period which is a time period corresponding to the beating based on the extracted fetal electrocardiogram base signal $u_\theta(\tau)$ at every beating of the heart of the fetus CB.

First, the rotation angle estimation unit 201 estimates some time point (for example, a time point in the middle of the time period) in a time period when a state where an absolute value of a value (in the example, potential) of the fetal electrocardiogram base signal $u_\theta(\tau)$ is smaller than a predetermined first threshold value is continuously maintained for longer than a predetermined first threshold value time as the boundary time point.

Next, the rotation angle estimation unit 201 acquires a maximum peak time point $\tau_{max0}$ which is a time point when the fetal electrocardiogram base signal $u_\theta(\tau)$ has a maximum value in a time period between consecutive two boundary time points among the estimated boundary time points.

Then, the rotation angle estimation unit 201 estimates the time period which starts at a time point which is a time of a half of the beating cycle earlier than the maximum peak time point $\tau_{max0}$ and ends at a time point which is a time of a half of the beating cycle later than the maximum peak time point $\tau_{max0}$ as the beating time period. For example, the beating cycle may be acquired by taking autocorrelation to the fetal electrocardiogram base signal $u_\theta(\tau)$.

By doing so, the rotation angle estimation unit 201 estimates the beating time period at every beating of the heart of the fetus CB.

Next, the rotation angle estimation unit 201 estimates the rotation angle θ for each of the estimated beating time periods.

In the example, the rotation angle estimation unit 201 stores a relationship (first relationship) between the rotation angle and a signal feature amount in advance.

In the example, the signal feature amount is a parameter calculated based on the maximum and minimum values of the fetal electrocardiogram base signal in a QRS wave time period which is a time period corresponding to the QRS wave among the beating time periods. The QRS wave is configured with a Q wave, an R wave, and S wave.

In the example, the signal feature amount R(θ) is expressed by Mathematical Formula 2. Herein, $\tau_{max}(\theta)$ denotes a time point (QRS wave time period maximum peak time point) when the fetal electrocardiogram base signal has a maximum value in the QRS wave time period. In addition, $\tau_{min}(\theta)$ denotes a time point (QRS wave time period minimum peak time point) when the fetal electrocardiogram base signal has a minimum value in the QRS wave time period. The QRS wave time period is an example of the target time period.

$$R(\theta) = \frac{u_\theta(\tau_{max}(\theta))}{u_\theta(\tau_{max}(\theta)) - u_\theta(\tau_{min}(\theta))}$$ [Mathematical Formula 2]

In the example, the QRS wave time period maximum peak time point $\tau_{max}(\theta)$ is expressed by Mathematical Formula 3, and the QRS wave time period minimum peak time point $\tau_{min}(\theta)$ is expressed by Mathematical Formula 4. Herein, $T_{QRS}$ denotes a length of the QRS wave time period. In the example, $T_{QRS}$ is set to a value obtained by multiplying the beating cycle with a predetermined coefficient (for example, ⅕).

$$\tau_{max}(\theta) = \underset{\tau_{max0}-\frac{T_{QRS}}{2}<\tau<\tau_{max0}+\frac{T_{QRS}}{2}}{\operatorname{argmax}} (u_\theta(\tau))$$ [Mathematical Formula 3]

$$\tau_{min}(\theta) = \underset{\tau_{max0}-\frac{T_{QRS}}{2}<\tau<\tau_{max0}+\frac{T_{QRS}}{2}}{\operatorname{argmin}} (u_\theta(\tau))$$ [Mathematical Formula 4]

In the example, the first relationship is determined based on reference signals (reference fetal electrocardiogram signals) of the fetal electrocardiogram signal expressed by Mathematical Formulas 5 to 7. $ECG_{x0}(\tau)$ denotes a reference fetal electrocardiogram signal of the case where the fetus CB is seen in the negative direction of the x axis. $ECG_{y0}(\tau)$ denotes a reference fetal electrocardiogram signal of the case where the fetus CB is seen in the negative direction of the y axis. $ECG_{z0}(\tau)$ denotes a reference fetal electrocardiogram signal of the case where the fetus CB is seen in the negative direction of the z axis.

$$ECG_{x0}(\tau) = \sum_i \alpha_i^x \exp\left[-\frac{(\tau - \tau_i^x)^2}{2(b_i^x)^2}\right] \quad \text{[Mathematical Formula 5]}$$

$$ECG_{y0}(\tau) = \sum_i \alpha_i^y \exp\left[-\frac{(\tau - \tau_i^y)^2}{2(b_i^y)^2}\right] \quad \text{[Mathematical Formula 6]}$$

$$ECG_{z0}(\tau) = \sum_i \alpha_i^z \exp\left[-\frac{(\tau - \tau_i^z)^2}{2(b_i^z)^2}\right] \quad \text{[Mathematical Formula 7]}$$

Figure 6:
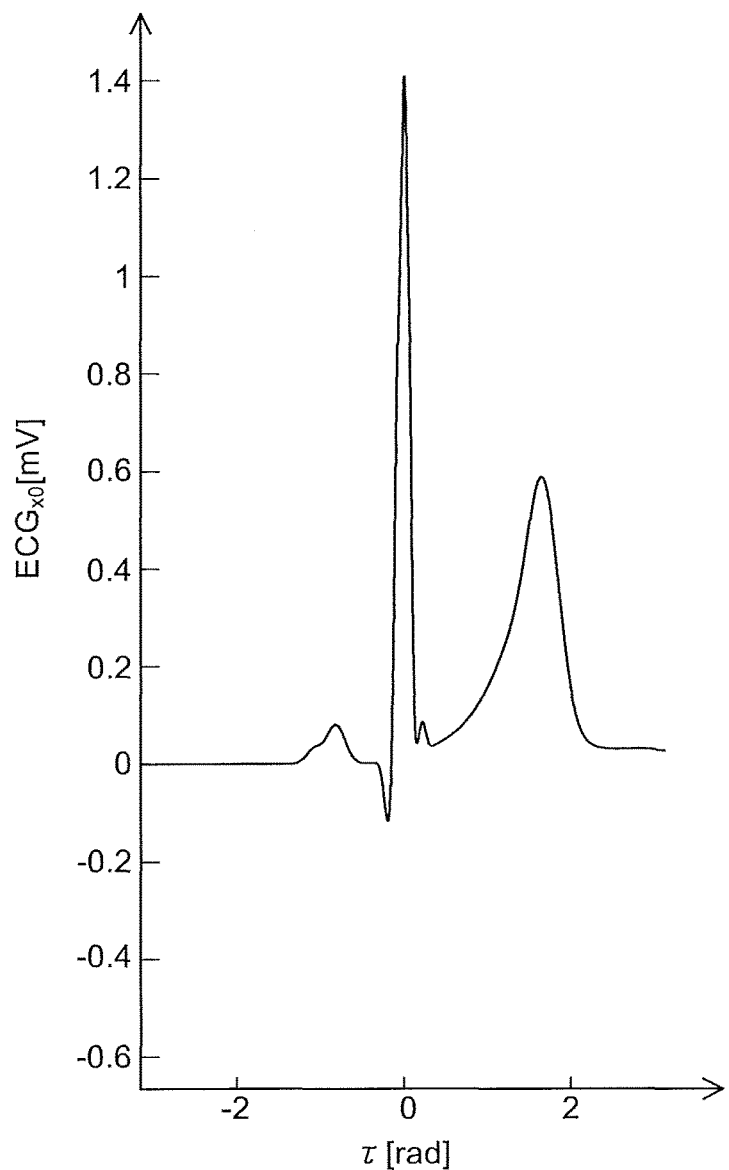
FIG. 6 is a graph illustrating an example of a reference fetal electrocardiogram signal used by the fetal state estimation apparatus illustrated in FIG. 3.
Figure 7:
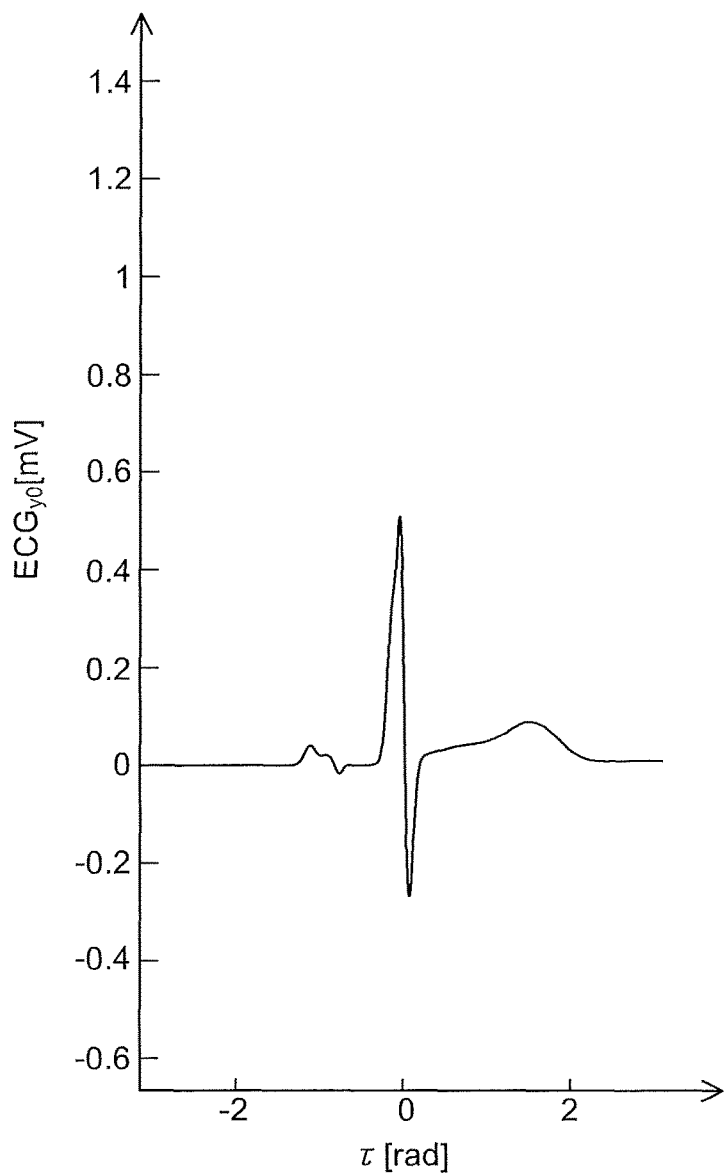
FIG. 7 is a graph illustrating an example of a reference fetal electrocardiogram signal used by the fetal state estimation apparatus illustrated in FIG. 3.
Figure 8:
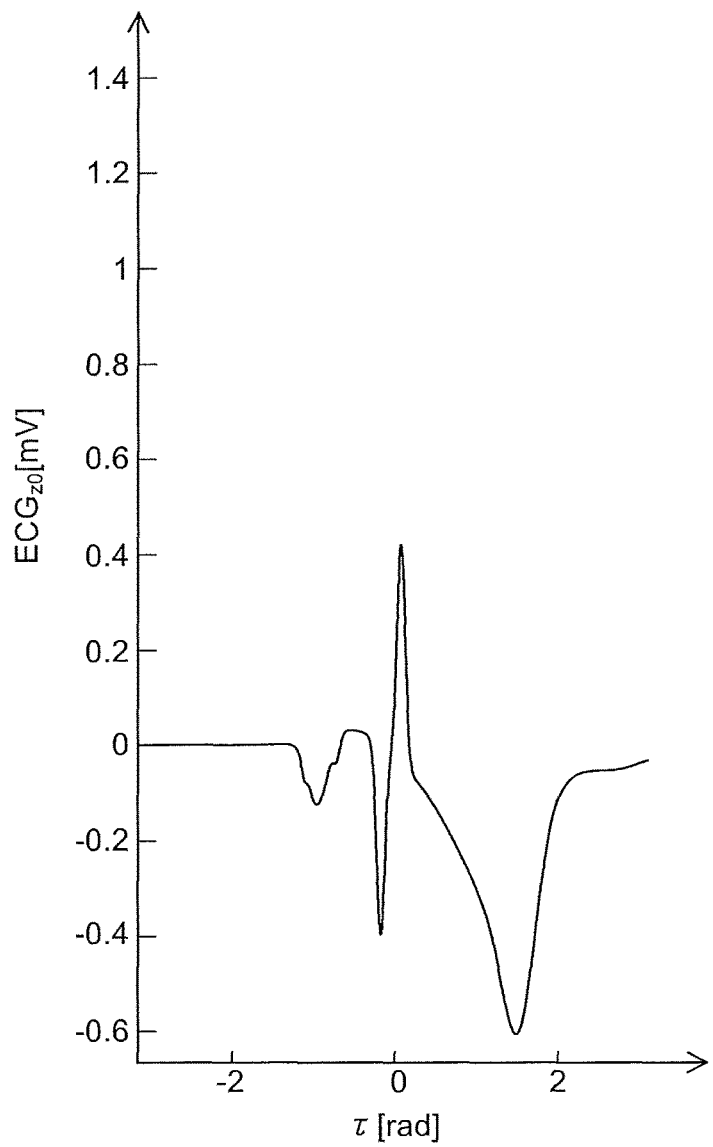
FIG. 8 is a graph illustrating an example of a reference fetal electrocardiogram signal used by the fetal state estimation apparatus illustrated in FIG. 3.

In the example, as illustrated in Mathematical Formulas 5 to 7, the reference fetal electrocardiogram signal is expressed by a sum of Gauss functions. Herein, $\alpha_i^x$, $\tau_i^x$, $b_i^x$, $\alpha_i^y$, $\tau_i^y$, $b_i^y$, $\alpha_i^z$, $\tau_i^z$, and $b_i^z$ are parameters specifying Gauss functions. In the example, as illustrated in FIGS. 6 to 8, an electrocardiogram signal disclosed in Non-Patent Literature 1 (R. Sameni, G. D. Clifford, C. Jutten, M. B. Shamsollahi, "Multichannel ECG and noise modeling: Application to maternal and fetal ECG signals", EURASIP Journal on Advances in Signal Processing, 2007, Article ID 43407) is used as a reference fetal electrocardiogram signal.

Figures 9A, 9B:
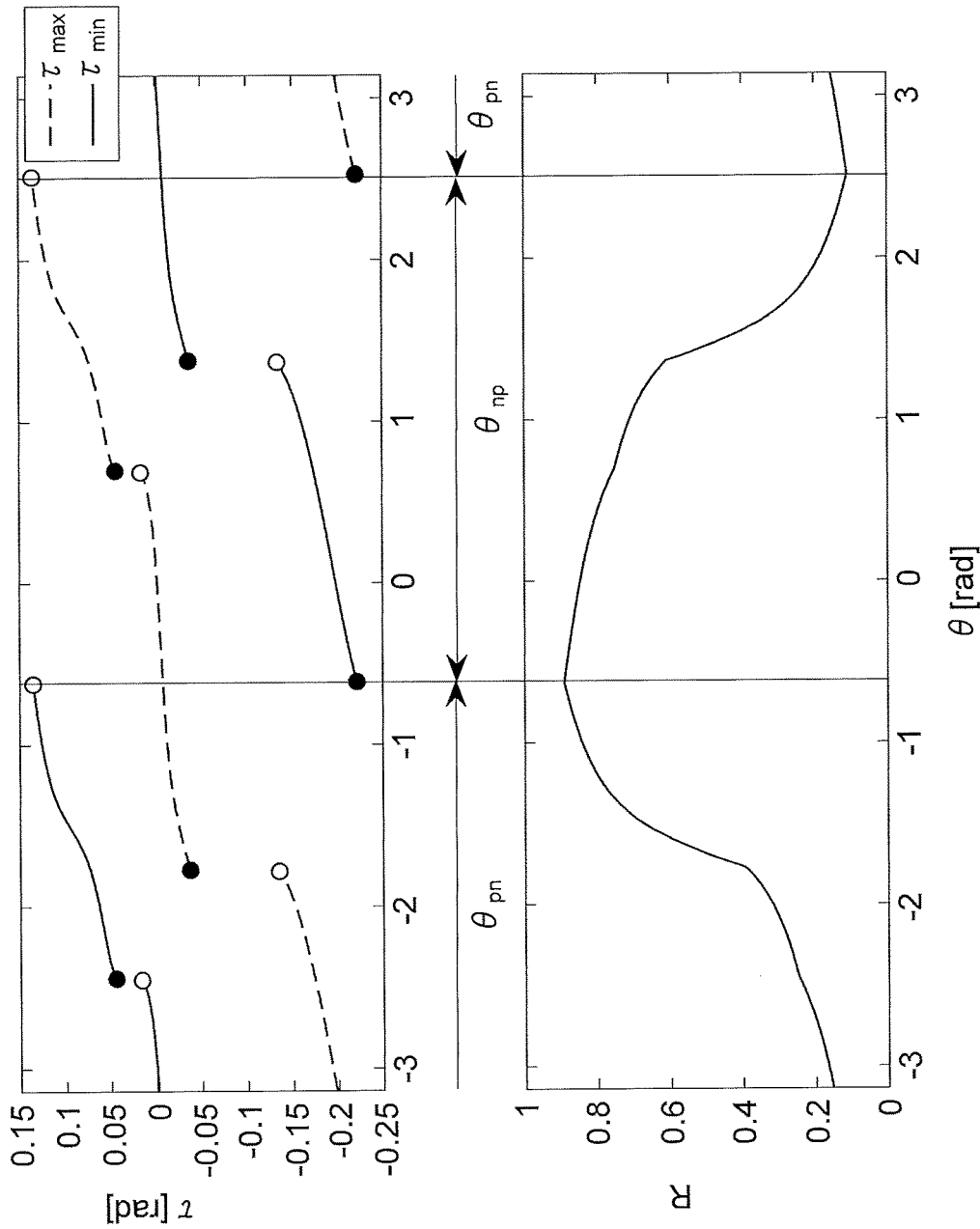
FIGS. 9(A) and 9(B) are graphs illustrating an example of a first relationship stored in the fetal state estimation apparatus illustrated in FIG. 3.

Therefore, the first relationship for the above-described reference fetal electrocardiogram signal is determined so as to be expressed by FIGS. 9(A) and 9(B). In FIG. 9(A), a relationship between the rotation angle θ and the QRS wave time period maximum peak time point $\tau_{max}(\theta)$ is indicated by a broken line, and a relationship between the rotation angle θ and the QRS wave time period minimum peak time point $\tau_{min}(\theta)$ is indicated by a solid line. In FIG. 9(B), a relationship between the rotation angle θ and the signal feature amount $R(\theta)$ is indicated by a solid line.

As illustrated in FIG. 9(A), there exist a range (minimum peak preceding range) $\theta_{np}$ of the rotation angle θ where the QRS wave time period maximum peak time point $\tau_{max}(\theta)$ becomes larger than the QRS wave time period minimum peak time point $\tau_{min}(\theta)$ and a range (maximum peak preceding range) $\theta_{pn}$ of the rotation angle θ where the QRS wave time period maximum peak time point $\tau_{max}(\theta)$ becomes smaller than the QRS wave time period minimum peak time point $\tau_{min}(\theta)$.

In addition, as illustrated in FIG. 9(B), in the minimum peak preceding range $\theta_{np}$, the rotation angle θ and the signal feature amount $R(\theta)$ are in one-to-one correspondence to each other. Similarly, in the maximum peak preceding range $\theta_{pn}$, the rotation angle θ and the signal feature amount $R(\theta)$ are in one-to-one correspondence to each other.

It is to be noted that the first relationship may be determined based on empirical rules.

The rotation angle estimation unit 201 acquires, for each of the estimated beating time periods, the QRS wave time period maximum peak time point $\tau_{max}(\theta)$ and the QRS wave time period minimum peak time point $\tau_{min}(\theta)$ based on the fetal electrocardiogram base signal $u_\theta(\tau)$.

Furthermore, the rotation angle estimation unit 201 calculates, for each of the estimated beating time periods, the signal feature amount $R(\theta)$ based on the acquired QRS wave time period maximum peak time point $\tau_{max}(\theta)$, the acquired QRS wave time period minimum peak time point $\tau_{min}(\theta)$, and the fetal electrocardiogram base signal $u_\theta(\tau)$.

In addition, the rotation angle estimation unit 201 estimates, for each of the estimated beating time periods, the rotation angle θ based on the stored first relationship and the calculated signal feature amount $R(\theta)$.

More specifically, in the case where the acquired QRS wave time period maximum peak time point $\tau_{max}(\theta)$ is larger than the acquired QRS wave time period minimum peak time point $\tau_{min}(\theta)$, the rotation angle estimation unit 201 estimates the rotation angle θ based on a portion corresponding to the minimum peak preceding range $\theta_{np}$ in the stored first relationship and the calculated signal feature amount $R(\theta)$. In addition, in the case where the acquired QRS wave time period maximum peak time point $\tau_{max}(\theta)$ is smaller than the acquired QRS wave time period minimum peak time point $\tau_{min}(\theta)$, the rotation angle estimation unit 201 estimates the rotation angle θ based on a portion corresponding to the maximum peak preceding range $\downarrow_{pn}$ in the stored first relationship and the calculated signal feature amount $R(\theta)$.

By doing so, the rotation angle estimation unit 201 estimates the rotation angle θ at every beating time period.

Figure 10:
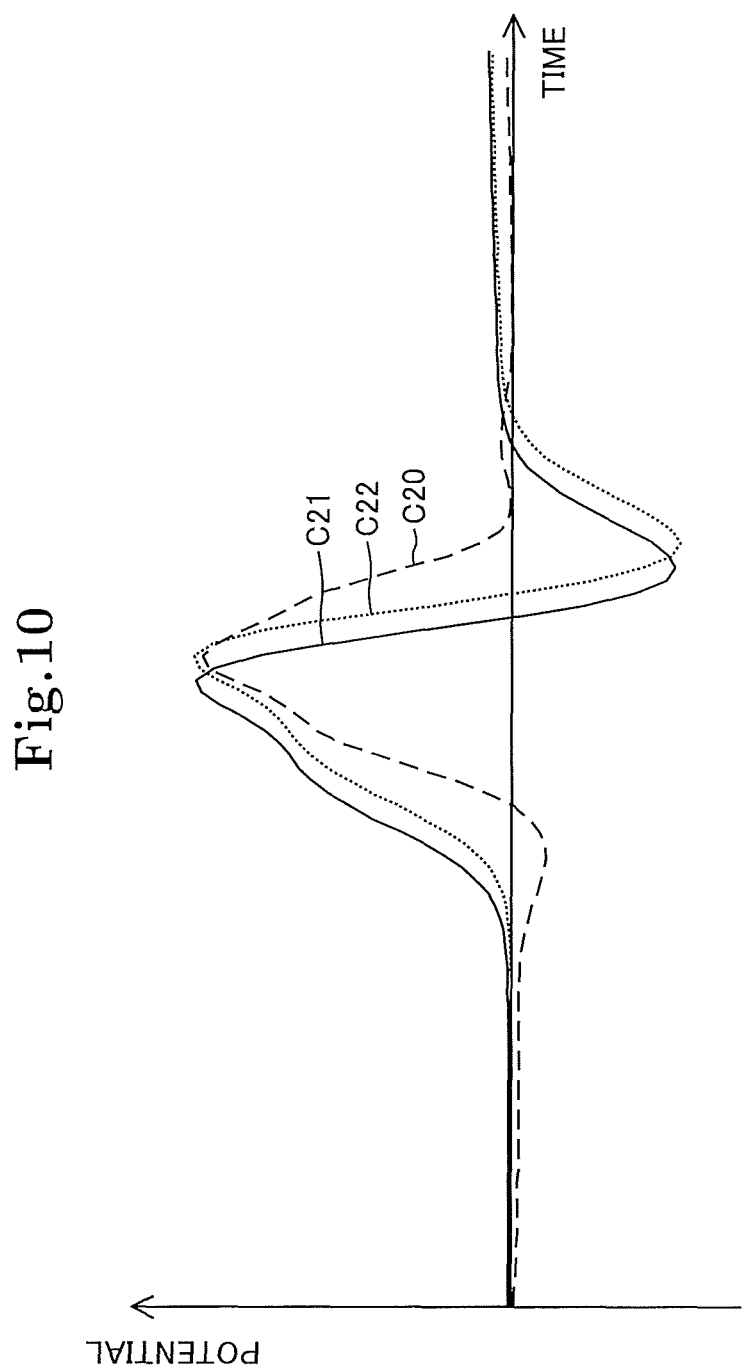
FIG. 10 is a graph illustrating an example of a change in maximum peak time point of a reference fetal electrocardiogram signal according to a rotation angle.

As described above, the maximum peak time point $\tau_{max0}$ in the fetal electrocardiogram base signal is changed according to the rotation angle θ. In FIG. 10, a broken curve C20 represents a reference fetal electrocardiogram signal of the case where the rotation angle is 0 (the case where the fetus CB is seen in the negative direction of the x axis), and a solid curve C21 represents a reference fetal electrocardiogram signal of the case where the rotation angle is different from 0. In this manner, a difference between the time point which is to be the center of the beating time period estimated by the rotation angle estimation unit 201 and the time point which is to be the center of the actual beating time period may be relatively large.

Therefore, the fetal movement estimation unit 202 re-estimates, for each of the estimated beating time periods, the time point which is to be the center of the beating time period based on the rotation angle θ estimated by the rotation angle estimation unit 201 and re-estimates the beating time period based on the re-estimated time point. In FIG. 10, a dotted curve C22 is a curve obtained by translating the curve C21 by a correction amount of the time point which is to be the center of the beating time period in the time axis.

The re-estimation of the time point which is to be the center of the beating time period will be described.

In the example, the fetal movement estimation unit 202 stores a relationship (second relationship) between the rotation angle and the rate of change in maximum peak time point in advance.

In the example, the rate of change in maximum peak time point is a parameter calculated based on the QRS wave time period maximum peak time point $\tau_{max}(\theta)$ of the case where the rotation angle is θ and the QRS wave time period maximum peak time point $\tau_{max}(0)$ of the case where the rotation angle is 0. In the example, the rate of change in maximum peak time point $S(\theta)$ is expressed by Mathematical Formula 8.

$$S(\theta) = \frac{\tau_{max}(\theta) - \tau_{max}(0)}{\tau_{max}(\theta) - \tau_{min}(\theta)} \quad \text{[Mathematical Formula 8]}$$

Figure 11:
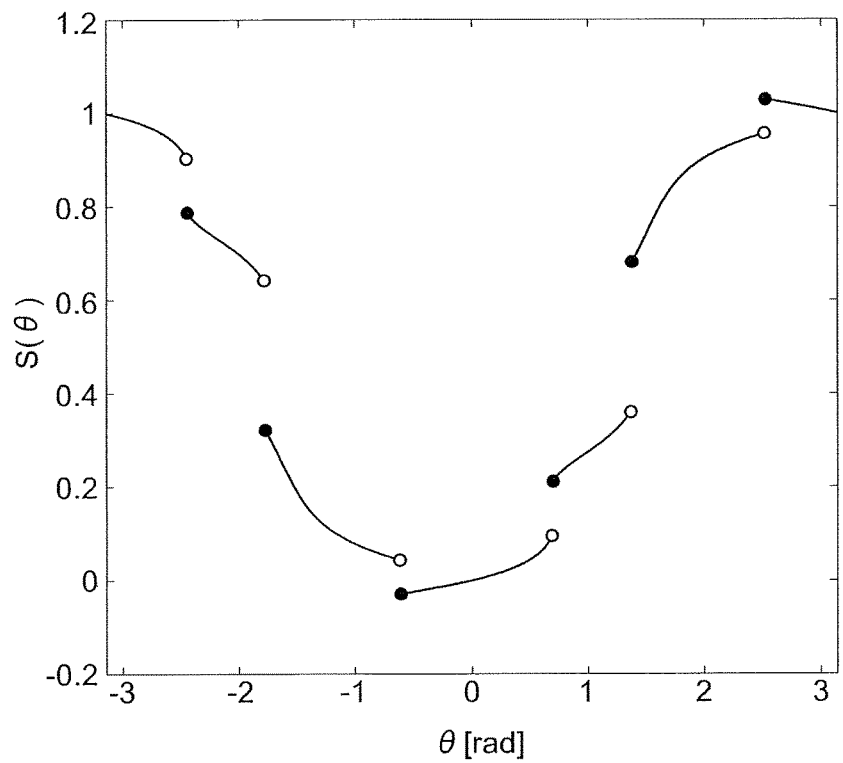
FIG. 11 is a graph illustrating an example of a second relationship stored in the fetal state estimation apparatus illustrated in FIG. 3.

In the example, the second relationship is determined based on the reference fetal electrocardiogram signal expressed by the above-described Mathematical Formulas 5 to 7. Therefore, the second relationship is determined as illustrated in FIG. 11.

It is to be noted that the second relationship may be determined based on empirical rules.

The fetal movement estimation unit 202 acquires, for each of the beating time periods estimated by the rotation angle estimation unit 201, the rate of change in maximum peak time point $S(\theta)$ based on the rotation angle $\theta$ estimated by the rotation angle estimation unit 201 and the stored second relationship.

Next, the fetal movement estimation unit 202 calculates, for each of the beating time periods estimated by the rotation angle estimation unit 201, the QRS wave time period maximum peak time point $\tau_{max}(0)$ of the case where the rotation angle is 0 based on the acquired rate of change in maximum peak time point $S(\theta)$ and Mathematical Formula 9. The QRS wave time period maximum peak time point $\tau_{max}(0)$ is an example of the maximum value time point.

$$\tau_{max}(0)=\tau_{max}(\theta)-S(\theta)\cdot(\tau_{max}(\theta)-\tau_{min}(\theta)) \quad \text{[Mathematical Formula 9]}$$

The fetal movement estimation unit 202 estimates, for each of the beating time periods estimated by the rotation angle estimation unit 201, the calculated QRS wave time period maximum peak time point $\tau_{max}(0)$ as a time point which is to be the center of the beating time period.

By doing so, the fetal movement estimation unit 202 re-estimates the time point which is to be the center of the beating time period.

Then, the fetal movement estimation unit 202 re-estimates the time period, which starts at a time point which is a time of a half of the beating cycle earlier than the QRS wave time period maximum peak time point $\tau_{max}(0)$ and ends at a time point which is a time of a half of the beating cycle later than the QRS wave time period maximum peak time point $\tau_{max}(0)$, as the beating time period for each of the beating time periods estimated by the rotation angle estimation unit 201.

Next, the fetal movement estimation unit 202 estimates the electrocardiogram signal (fetal electrocardiogram signal) of the fetus CB with respect to a predetermined reference rotation angle based on the re-estimated beating time period, the rotation angle $\theta$ estimated by the rotation angle estimation unit 201, and the fetal electrocardiogram base signal.

In the example, the fetal movement estimation unit 202 estimates a first fetal electrocardiogram signal $ECG_x(\tau)$ of the case where the rotation angle is 0 and a second fetal electrocardiogram signal $ECG_y(\tau)$ of the case where the rotation angle is $3\pi/2$. The first fetal electrocardiogram signal $ECG_x(\tau)$ is an example of the electrocardiogram signal of the fetus CB with respect to the first reference rotation angle of 0. The second fetal electrocardiogram signal $ECG_y(\tau)$ is an example of the electrocardiogram signal of the fetus CB with respect to the second reference rotation angle of $3\pi/2$.

In the fetal electrocardiogram base signal, p signal values included in each of the re-estimated beating time periods may be analyzed as a p-dimensional vector. p denotes a natural number and indicates the number of samples. The p signal values included in each of a plurality of the beating time periods are expressed by one point in a p-dimensional space. Therefore, the fetal electrocardiogram base signal constitutes a set of points, of which number is equal to the number of beating time periods included in the fetal electrocardiogram base signal, in the p-dimensional space.

The fetal movement estimation unit 202 acquires first and second main component vectors which are perpendicular to each other by performing a main component analysis on a point set indicating the fetal electrocardiogram base signals in the p-dimensional space.

Next, the fetal movement estimation unit 202 acquires, for each of the re-estimated beating time periods, the first main component $u_{\theta_1}$ and the second main component $u_{\theta_2}$ of the fetal electrocardiogram base signal in the beating time period. The first main component $u_{\theta_1}$ is a component in the direction along the first main component vector in the fetal electrocardiogram base signal in the beating time period. The second main component $u_{\theta_2}$ is a component in the direction along the second main component vector in the fetal electrocardiogram base signal in the beating time period.

Furthermore, the fetal movement estimation unit 202 estimates a first rotation angle $\theta_1$ corresponding to the first main component vector and a second rotation angle $\theta_2$ corresponding to the second main component vector. In the example, the fetal movement estimation unit 202 acquires a QRS wave time period maximum peak time point $\tau_{max}(\theta)$ and a QRS wave time period minimum peak time point $\tau_{min}(\theta)$ for a signal expressed by the first main component vector and calculates a signal feature amount $R(\theta)$ based on the QRS wave time period maximum peak time point $\tau_{max}(\theta)$ and the QRS wave time period minimum peak time point $\tau_{min}(\theta)$. In addition, the fetal movement estimation unit 202 estimates the first rotation angle $\theta_1$ based on the stored first relationship and the calculated signal feature amount $R(\theta)$. Similarly, the fetal movement estimation unit 202 estimates the second rotation angle $\theta_2$ for a signal expressed by the second main component vector.

The first main component $u_{\theta_1}$ and the second main component $u_{\theta_2}$ are normalized so as to constitute a unit vector. Therefore, the fetal movement estimation unit 202 performs scaling based on Mathematical Formulas 10 and 11. Herein, E [X] denotes an average of X. V[X] denotes a variance of X. $ECG_{\theta_{10}}$ denotes a reference fetal electrocardiogram signal of the case in which the fetus CB is seen in the direction obtained by rotating the negative direction of the x axis by the first rotation angle $\theta_1$. $ECG_{\theta_{20}}$ denotes a reference fetal electrocardiogram signal of the case in which the fetus CB is seen in the direction obtained by rotating the negative direction of the x axis by the second rotation angle $\theta_2$.

$$ECG_{\theta 1}=u_{\theta 1}\sqrt{V[ECG_{\theta 10}]}+E[ECG_{\theta 10}] \quad \text{[Mathematical Formula 10]}$$

$$ECG_{\theta 2}=u_{\theta 2}\sqrt{V[ECG_{\theta 20}]}+E[ECG_{\theta 20}] \quad \text{[Mathematical Formula 11]}$$

The fetal movement estimation unit 202 estimates the first and second fetal electrocardiogram signals $ECG_x(\tau)$ and $ECG_y(\tau)$ based on the first and second main components $ECG_{\theta_1}$ and $ECG_{\theta_2}$ after the scaling, the estimated first and second rotation angles $\theta_1$ and $\theta_2$, and Mathematical Formula 12.

$$\begin{bmatrix} ECG_x(\tau) \\ ECG_y(\tau) \end{bmatrix} = \begin{bmatrix} \cos(\theta_1) & -\sin(\theta_1) \\ \cos(\theta_2) & -\sin(\theta_2) \end{bmatrix}^{-1} \cdot \begin{bmatrix} ECG_{\theta 1}(\tau) \\ ECG_{\theta 2}(\tau) \end{bmatrix} \quad \text{[Mathematical Formula 12]}$$

Furthermore, the fetal movement estimation unit 202 estimates the fetal movement which is movement of the fetus based on the fetal electrocardiogram base signal and the rotation angle θ estimated by the rotation angle estimation unit 201.

Figure 12:
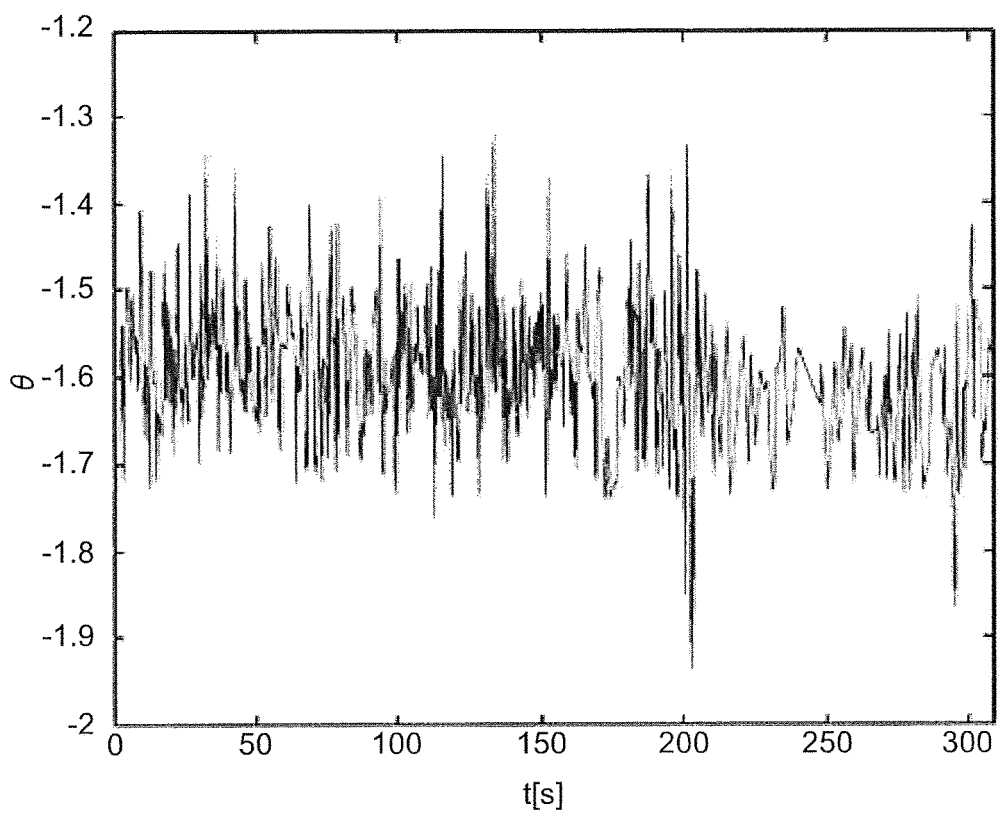
FIG. 12 is a graph illustrating an example of a change in rotation angle of a fetus with respect to a maternal body according to time.

FIG. 12 illustrates an example of a change in rotation angle θ according to time. In the example, the fetal movement estimation unit 202 calculates a variance of the rotation angle θ for each of the beating time periods at every time period having a predetermined first determination time. Furthermore, at every time period, in the case where the calculated variance is larger than a predetermined first variance threshold value, the fetal movement estimation unit 202 estimates that the rotational movement is performed in the time period; and in the case where the calculated variance is smaller than the first variance threshold value, the fetal movement estimation unit 202 estimates that the rotational movement is not performed in the time period. The variance of the rotation angle θ is an example of a first variation parameter indicating a variation of the rotation angle θ. The first variance threshold value is an example of a first variation threshold value.

In addition, in the example, the fetal movement estimation unit 202 estimates the existence of translational movement with respect to the abdominal wall of the maternal body MB among the fetal movements based on a change in magnitude of peak of the R wave in the fetal electrocardiogram base signal. The R wave is an example of a reference wave. For example, in many cases, a magnitude of peak of an R wave in the fetal electrocardiogram base signal is the maximum value in each of the beating time periods.

Figure 13:
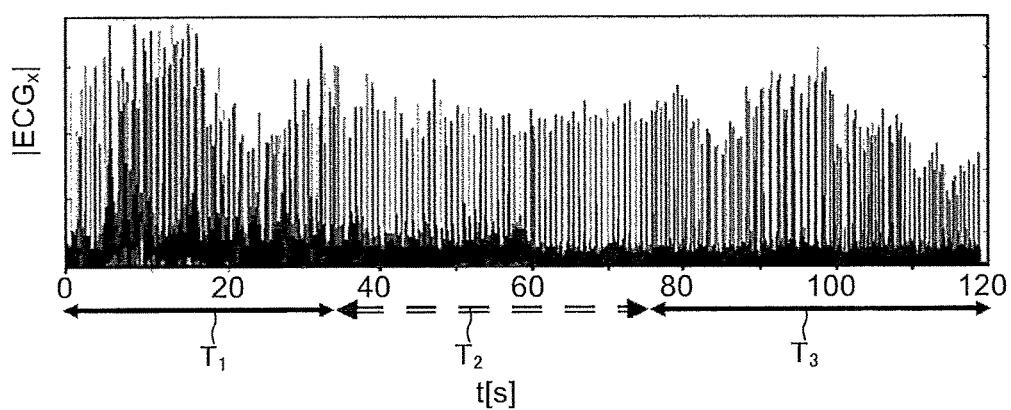
FIG. 13 is a graph illustrating an example of a change in absolute value of a first fetal electrocardiogram signal according to time.

FIG. 13 illustrates an example of a change in absolute value of the fetal electrocardiogram base signal according to time. As illustrated in FIG. 13, in many cases, the translational movement is performed in time periods $T_1$ and $T_3$ when a change in maximum value of the fetal electrocardiogram base signal in each of the beating time periods is relatively large. In addition, in many cases, the translational movement is not performed in time period $T_2$ when a change in maximum value of the fetal electrocardiogram base signal in each of the beating time periods is relatively small.

In the example, the fetal movement estimation unit 202 calculates a variance of the maximum value of the fetal electrocardiogram base signal in each of the beating time periods at every time period having a predetermined second determination time. Furthermore, at every time period having the predetermined second determination time, in the case where the fetal movement estimation unit 202 estimates that the rotational movement is not performed in the time period and the calculated variance is larger than a predetermined second variance threshold value, the fetal movement estimation unit 202 estimates that the translational movement is performed in the time period; in the case where the fetal movement estimation unit 202 estimates that the rotational movement is performed in the time period, the fetal movement estimation unit 202 estimates that the translational movement is not performed in the time period; and in the case where the calculated variance is smaller than the second variance threshold value, the fetal movement estimation unit 202 estimates that the translational movement is not performed in the time period.

The fetal movement estimation unit 202 may estimate the existence of translational movement based on a change in magnitude of peak of a specific wave different from the R wave instead of the R wave.

The fetal movement estimation unit 202 may estimate the strength of translational movement based on an amount of a change in maximum value of the fetal electrocardiogram base signal at each of the beating time periods.

The fetal movement estimation unit 202 may generate a vector electrocardiogram based on the estimated first fetal electrocardiogram signal $ECG_x(\tau)$ and the estimated second fetal electrocardiogram signal $ECG_y(\tau)$.

In addition, although the fetal movement estimation unit 202 estimates the existence of translational movement based on the fetal electrocardiogram base signal, the fetal movement estimation unit 202 may estimate the existence of translational movement based on a fetal electrocardiogram signal with respect to a predetermined reference rotation angle which is the first fetal electrocardiogram signal $ECG_x(\tau)$, the second fetal electrocardiogram signal $ECG_y(\tau)$, or the like.

The output unit 30 outputs information (for example, a graph) indicating a change in the rotation angle θ estimated by the rotation angle estimation unit 201, the existence of rotational movement estimated by the fetal movement estimation unit 202, and the existence of translational movement estimated by the fetal movement estimation unit 202 with respect to time (for example, displays the information on a display). In addition to outputting the information or instead of outputting the information, the output unit 30 may store the information in a storage device.

It is to be noted that the fetal movement estimation unit 202 may omit to estimate the first fetal electrocardiogram signal $ECG_x(\tau)$ and the second fetal electrocardiogram signal $ECG_y(\tau)$.

(Operations)

Next, operations of the above-described fetal state estimation apparatus 1 will be described with reference to FIG. 14.

First, the electrodes 11 to 15 are attached to a surface (for example, skin) MBS of the abdomen of a pregnant maternal body MB.

The fetal state estimation apparatus 1 extracts the fetal electrocardiogram base signal from the bio-potential signal measured by the measurement unit 10 using the ICA (Step S101 of FIG. 14).

Next, the fetal state estimation apparatus 1 estimates boundary time points and acquires the maximum peak time point $\tau_{max0}$ when the fetal electrocardiogram base signal $u_\theta(\tau)$ has a maximum value in a time period between consecutive two boundary time points among the estimated boundary time points (Step S102 of FIG. 14).

Then, the fetal state estimation apparatus 1 estimates the time period, which starts at a time point which is a time of a half of the beating cycle earlier than the maximum peak time point $\tau_{max0}$ and ends at a time point which is a time of a half of the beating cycle later than the maximum peak time point $\tau_{max0}$, as the beating time period (Step S103 of FIG. 14).

Next, the fetal state estimation apparatus 1 acquires the QRS wave time period maximum peak time point $\tau_{max}(\theta)$ and the QRS wave time period minimum peak time point $\tau_{min}(\theta)$ for each of the estimated beating time periods. Then, the fetal state estimation apparatus 1 calculates, for each of the estimated beating time periods, the signal feature amount $R(\theta)$ based on the acquired QRS wave time period maximum peak time point $\tau_{max}(\theta)$, the acquired QRS wave time period minimum peak time point $\tau_{min}(\theta)$, and the fetal electrocardiogram base signal $u_\theta(\tau)$ (Step S104 of FIG. 14).

Next, the fetal state estimation apparatus 1 estimates, for each of the estimated beating time periods, the rotation angle θ based on the stored first relationship and the calculated signal feature amount $R(\theta)$ (Step S105 of FIG. 14).

Then, the fetal state estimation apparatus 1 acquires, for each of the estimated beating time periods, the rate of change in maximum peak time point S(θ) based on the estimated rotation angle θ and the stored second relationship. Furthermore, the fetal state estimation apparatus 1 calculates, for each of the estimated beating time periods, the QRS wave time period maximum peak time point $\tau_{max}(\theta)$ of the case where the rotation angle is 0 based on the acquired rate of change in maximum peak time point S(θ). Next, the fetal state estimation apparatus 1 estimates the calculated QRS wave time period maximum peak time point $\tau_{max}(0)$ as the time point which is to be the center of the beating time period (Step S106 of FIG. 14).

Then, the fetal state estimation apparatus 1 re-estimates, for each of the estimated beating time periods, the time period, which starts at a time point which is a time of a half of the beating cycle earlier than the QRS wave time period maximum peak time point $\tau_{max}(\theta)$ and ends at a time point which is a time of a half of the beating cycle later than the QRS wave time period maximum peak time point $\tau_{max}(0)$, as the beating time period (Step S107 of FIG. 14).

Next, the fetal state estimation apparatus 1 estimates the fetal electrocardiogram signal with respect to the reference rotation angle based on the re-estimated beating time period, the estimated rotation angle θ, and the estimated fetal electrocardiogram base signal (Step S108 of FIG. 14). In the example, the fetal state estimation apparatus 1 estimates the first fetal electrocardiogram signal with respect to the first reference rotation angle and the second fetal electrocardiogram signal with respect to the second reference rotation angle.

The fetal state estimation apparatus 1 estimates the existence of rotational movement based on the estimated rotation angle θ. In addition, the fetal state estimation apparatus 1 estimates the existence of translational movement based on the estimated rotation angle θ and the fetal electrocardiogram signal (Step S109 of FIG. 14).

As described hereinbefore, the fetal state estimation apparatus 1 according to the first embodiment estimates the rotation angle of the fetus CB with respect to the maternal body MB at every beating of the heart of the fetus CB based on the potential signal indicating a change in potential on the surface MBS of the maternal body MB. In addition, the fetal state estimation apparatus 1 estimates the fetal movement, that is, the movement of the fetus CB based on the potential signal and the estimated rotation angle.

Accordingly, it is possible to estimate the fetal movement with high accuracy. For example, it is possible to estimate the existence of translational movement among the fetal movements with high accuracy.

In addition, the fetal state estimation apparatus 1 according to the first embodiment estimates the electrocardiogram base signal caused by the beating of the heart of the fetus CB. Furthermore, the fetal state estimation apparatus 1 estimates the existence of translational movement among the fetal movements with respect to the abdominal wall of the maternal body MB based on the magnitude of a peak of a predetermined reference wave in the estimated electrocardiogram base signal and the estimated rotation angle.

The change in distance between the abdominal wall of the maternal body MB and the fetus CB is represented well by the change in magnitude of peak of a specific wave. Therefore, according to the fetal state estimation apparatus 1 of the first embodiment, it is possible to estimate the existence of the translational movement among the fetal movements with high accuracy.

In addition, the fetal state estimation apparatus 1 according to the first embodiment calculates predetermined parameters based on the maximum and minimum values of the estimated electrocardiogram base signal in a predetermined target time period at every beating of the heart of the fetus CB. Furthermore, the fetal state estimation apparatus 1 estimates the rotation angle based on the calculated parameters at every beating of the heart of the fetus CB.

The rotation angle of the fetus CB with respect to the maternal body MB at every beating of the heat of the fetus CB is represented well by the relationship between the maximum and minimum values of the electrocardiogram base signal in the predetermined target time period. Therefore, according to the fetal state estimation apparatus 1 of the first embodiment, it is possible to estimate the rotation angle of the fetus CB with respect to the maternal body MB with high accuracy.

Furthermore, the fetal state estimation apparatus 1 according to the first embodiment estimates the maximum value time point which is a time point when the electrocardiogram signal of the fetus CB with respect to a predetermined reference rotation angle has a maximum value based on a time point when the estimated electrocardiogram base signal has a maximum value in the target time period and the estimated rotation angle at every beating of the heart of the fetus CB. In addition, the fetal state estimation apparatus 1 estimates the fetal movement based on the estimated maximum value time point, the estimated rotation angle, and the estimated electrocardiogram base signal.

The appearing shape of the change in electromotive force of heart of the fetus CB in the electrocardiogram base signal is changed according to the rotation angle of the fetus CB with respect to the maternal body MB. Therefore, according to the fetal state estimation apparatus 1 of the first embodiment, it is possible to estimate the maximum value time point when the electrocardiogram signal has a maximum value with high accuracy at every beating of the heart of the fetus CB. As a result, it is possible to estimate the time period when the rotational movement is performed with high accuracy based on the estimated maximum value time point. Accordingly, it is possible to estimate the fetal movement with high accuracy.

In addition, the fetal state estimation apparatus 1 according to the first embodiment estimates the electrocardiogram base signal by using an Independent Component Analysis.

Accordingly, it is possible to estimate the electrocardiogram base signal with high accuracy.

Second Embodiment

Next, a fetal state estimation apparatus according to a second embodiment of the present invention will be described. The fetal state estimation apparatus according to the second embodiment is different from the fetal state estimation apparatus according to the first embodiment in that the fetal movement is estimated without the estimation of the fetal electrocardiogram signal with respect to the reference rotation angle. Hereinafter, the difference will be mainly described. In the description of the second embodiment, the components denoted by the same reference numerals as those of the first embodiment are the same as or almost the same as the components of the first embodiment.

The fetal movement estimation unit 202 of the fetal state estimation apparatus 1 according to the second embodiment estimates the maximum value of the fetal electrocardiogram base signal in the QRS wave time period of the case where the rotation angle is 0 without estimation of the fetal electrocardiogram signal with respect to the reference rotation angle.

More specifically, the fetal movement estimation unit 202 stores a relationship (third relationship) between the rotation angle and the rate of chancre in maximum value in advance.

In the example, the rate of change in maximum value is a parameter calculated based on the maximum value $u_\theta(\tau_{max}(\theta))$ of the fetal electrocardiogram base signal in the QRS wave time period of the case where the rotation angle is $\theta$ and the maximum value $u_\theta(\tau_{max}(0))$ of the fetal electrocardiogram base signal in the QRS wave time period of the case where the rotation angle is 0. In the example, the rate of change in maximum value $T(\tau)$ is expressed by Mathematical Formula 13.

$$T(\theta) = \frac{u_\theta(\tau_{max}(\theta)) - u_0(\tau_{max}(0))}{u_\theta(\tau_{max}(\theta)) - u_\theta(\tau_{min}(\theta))} \qquad \text{[Mathematical Formula 13]}$$

In the example, the third relationship is determined based on the reference fetal electrocardiogram signal expressed by the above-described Mathematical Formulas 5 to 7. It is to be noted that the third relationship may be determined based on empirical rules.

The fetal movement estimation unit 202 acquires, for each of the beating time periods estimated by the rotation angle estimation unit 201, the rate of change in maximum value $T(\theta)$ based on the rotation angle $\theta$ estimated by the rotation angle estimation unit 201 and the stored third relationship.

Next, the fetal movement estimation unit 202 calculates, for each of the beating time periods estimated by the rotation angle estimation unit 201, the maximum value $u_0(\theta_{max}(0))$ of the fetal electrocardiogram base signal in the QRS wave time period of the case where the rotation angle is 0 based on the acquired rate of change in maximum value $T(\theta)$, the maximum value $u_\theta(\tau_{max}(\theta))$ of the fetal electrocardiogram base signal in the QRS wave time period of the case where the rotation angle is $\theta$, the minimum value $u_\theta(\tau_{min}(\theta))$ of the fetal electrocardiogram base signal in the QRS wave time period of the case where the rotation angle is $\theta$, and Mathematical Formula 14. The maximum value $u_0(\tau_{max}(0))$ of the fetal electrocardiogram base signal in the QRS wave time period is an example of a magnitude of peak of the R wave. The R wave is an example of a reference wave.

$$u_0(\tau_{max}(0)) = u_\theta(\tau_{max}(\theta)) - T(\theta)\{u_\theta(\tau_{max}(\theta)) - u_\theta(\tau_{min}(\theta))\} \qquad \text{[Mathematical Formula 14]}$$

Furthermore, the fetal movement estimation unit 202 estimates the existence of translational movement with respect to the abdominal wall of the maternal body MB among the fetal movements based on the change in the calculated maximum value $u_0(\tau_{max}(0))$ of the fetal electrocardiogram base signal instead of the change in magnitude of peak of the R wave in the fetal electrocardiogram base signal.

The operations of the fetal state estimation apparatus 1 according to the second embodiment are the same as those of the fetal state estimation apparatus 1 according to the first embodiment. Therefore, the fetal state estimation apparatus 1 according to the second embodiment can obtain the same functions and effects as those of the fetal state estimation apparatus 1 according to the first embodiment.

Hereinbefore, while the present invention is described with reference to the above-described embodiments, the present invention is not limited to the above-described embodiments. It may be understood by the skilled in the related art that various changes may be available to configurations and details of the present invention within the scope of the present invention.

In addition, any combination of the above-described embodiments and modified examples may be employed as other modified examples of the above-described embodiments within the scope without departing from the spirit of the present invention.

What is claimed is:

1. A fetal state estimation apparatus comprising a processor,
   the processor configured to:
   estimate a rotation angle of a fetus in a maternal body with respect to the maternal body at every beating of a heart of the fetus based on a potential signal indicating a change in potential on a surface of the maternal body; and
   estimate a fetal movement which is a movement of the fetus based on the potential signal and the estimated rotation angle, wherein
   the estimating of the rotation angle comprises estimating an electrocardiogram base signal caused by the beating of the heart of the fetus; and
   the estimating of the fetal movement comprises estimating existence of a translational movement with respect to an abdominal wall of the maternal body among the fetal movements based on a predetermined beating time period, a magnitude of a peak of a predetermined reference wave in the estimated electrocardiogram base signal, and the estimated rotation angle, the predetermined beating time period being estimated based on the estimated electrocardiogram base signal.

2. The fetal state estimation apparatus according to claim 1, wherein the estimating of the fetal movement comprises estimating that the translational movement with respect to the abdominal wall of the maternal body among the fetal movements is performed in a time period when a first variation parameter indicating a variation of the estimated rotation angle is smaller than a predetermined first variation threshold value and a second variation parameter indicating a variation of the magnitude of the peak is larger than a predetermined second variation threshold value.

3. The fetal state estimation apparatus according to claim 1, wherein the estimating of the rotation angle comprises:
   estimating an electrocardiogram base signal caused by the beating of the heart of the fetus;
   calculating a predetermined parameter based on maximum and minimum values of the estimated electrocardiogram base signal in a predetermined target time period at every beating of the heart of the fetus; and
   estimating the rotation angle based on the calculated parameter at every beating of the heart of the fetus.

4. The fetal state estimation apparatus according to claim 3, wherein the parameter is a value obtained by dividing the maximum value by a value obtained by subtracting the minimum value from the maximum value.

5. The fetal state estimation apparatus according to claim 3, wherein the estimating of the fetal movement comprises:
   estimating a maximum value time point which is a time point when the electrocardiogram signal of the fetus with respect to a predetermined reference rotation angle has a maximum value based on a time point when the estimated electrocardiogram base signal has a maximum value in the target time period and the estimated rotation angle at every beating of the heart of the fetus; and
   estimating the fetal movement based on the estimated maximum value time point, the estimated rotation angle, and the estimated electrocardiogram base signal.

6. The fetal state estimation apparatus according to claim 3, wherein the estimating of the rotation angle comprises estimating the electrocardiogram base signal by using an independent component analysis.

7. A non-transitory computer-readable medium that stores a fetal state estimating program for causing a computer to execute a process of estimating a state of a fetus in a maternal body based on a potential signal indicating a change in potential on a surface of the maternal body, the process comprising:
   estimating a rotation angle of the fetus with respect to the maternal body at every beating of a heart of the fetus based on the potential signal; and
   estimating a fetal movement which is a movement of the fetus based on the potential signal and the estimated rotation angle, wherein
   the estimating of the rotation angle comprises estimating an electrocardiogram base signal caused by the beating of the heart of the fetus; and
   the estimating of a fetal movement comprises estimating existence of a translational movement with respect to an abdominal wall of the maternal body among the fetal movements based on a predetermined beating time period, a magnitude of a peak of a predetermined reference wave in the estimated electrocardiogram base signal, and the estimated rotation angle, the predetermined beating time period being estimated based on the estimated electrocardiogram base signal.

8. The non-transitory computer-readable medium according to claim 7, wherein the estimating of the fetal movement comprises estimating that the translational movement with respect to the abdominal wall of the maternal body among the fetal movements is performed in a time period when a first variation parameter indicating a variation of the estimated rotation angle is smaller than a predetermined first variation threshold value and a second variation parameter indicating a variation of the magnitude of the peak is larger than a predetermined second variation threshold value.

9. The non-transitory computer-readable medium according to claim 7, wherein the estimating of the rotation angle comprises:
   estimating an electrocardiogram base signal caused by the beating of the heart of the fetus;
   calculating a predetermined parameter based on maximum and minimum values of the estimated electrocardiogram base signal in a predetermined target time period at every beating of the heart of the fetus; and
   estimating the rotation angle based on the calculated parameter at every beating of the heart of the fetus.

10. The non-transitory computer-readable medium according to claim 9, wherein the estimating of the fetal movement comprises:
   estimating a maximum value time point which is a time point when the electrocardiogram signal of the fetus with respect to a predetermined reference rotation angle has a maximum value based on a time point when the estimated electrocardiogram base signal has a maximum value in the target time period and the estimated rotation angle at every beating of the heart of the fetus; and
   estimating the fetal movement based on the estimated maximum value time point, the estimated rotation angle, and the estimated electrocardiogram base signal.

* * * * *